United States Patent [19]

Eldrige, Jr.

[11] Patent Number: 4,637,513

[45] Date of Patent: Jan. 20, 1987

[54] DISPOSABLE SURGICAL IMPLEMENT COLLECTOR

[75] Inventor: John D. Eldrige, Jr., Newport Beach, Calif.

[73] Assignee: Instranetics, Inc., Tustin, Calif.

[21] Appl. No.: 198,827

[22] Filed: Oct. 20, 1980

Related U.S. Application Data

[63] Continuation of Ser. No. 6,732, Jan. 26, 1979, abandoned, which is a continuation-in-part of Ser. No. 940,399, Sep. 8, 1978, abandoned.

[51] Int. Cl.$^4$ ............... A61B 17/06; B65D 85/24
[52] U.S. Cl. ................ 206/370; 206/63.3; 206/363; 206/380; 206/382; 206/459; 206/818
[58] Field of Search ........... 206/84, 564, 566, 380, 206/382, 383, 63.3, 523, 818, 370, 387, 459, 363; 264/321; 428/159, 160, 163, 166, 167, 170, 172; 220/339

[56] References Cited

U.S. PATENT DOCUMENTS

| | | | |
|---|---|---|---|
| D. 166,734 | 5/1952 | Chandler | 206/564 X |
| 2,784,757 | 3/1957 | Bosca et al. | 150/35 |
| 2,861,682 | 11/1958 | Hatcher | 206/566 X |
| 2,946,713 | 7/1960 | Dusina, Jr. et al. | 264/321 |
| 2,962,156 | 11/1960 | Adams | 206/564 X |
| 3,285,768 | 11/1966 | Habib | 428/160 |
| 3,356,092 | 12/1967 | Joa | 428/167 X |
| 3,360,179 | 12/1967 | Carstens | 217/35 |
| 3,370,117 | 2/1968 | Blue | 264/321 |
| 3,381,782 | 5/1968 | Ikelheimer | 217/35 X |
| 3,447,199 | 6/1969 | Trimble | 220/339 |
| 3,483,494 | 12/1969 | Cromie | 206/818 |
| 3,565,262 | 2/1971 | Sosalla | 206/564 X |
| 3,591,032 | 7/1971 | Baxter | 206/564 X |
| 3,616,155 | 10/1971 | Chavannes | 428/159 |
| 3,727,658 | 4/1973 | Eldridge, Jr. | 128/132 D X |
| 3,944,069 | 3/1976 | Eldridge, Jr. | 206/633 X |
| 4,008,802 | 2/1977 | Freitas | 206/63.3 |
| 4,054,206 | 10/1977 | Kobayashi et al. | 206/387 |
| 4,093,010 | 6/1978 | Hunley et al. | 206/523 |
| 4,151,913 | 5/1979 | Freitas | 206/633 X |

Primary Examiner—Allan N. Shoap
Attorney, Agent, or Firm—Knobbe, Martens, Olson & Bear

[57] ABSTRACT

A disposable surgical implement collector wherein a lamination of sponge plastic is provided at intervals with a series of spaced ribs, the ribs and adjacent portions of the lamination being depressed at intervals to form clearly marked channels dividing the ribs into a series of embossments which are numbered; each embossment adapted to receive a surgical needle or other small disposable surgical instrument; the sponge plastic lamination being bonded to a relatively rigid lamination provided with fold lines so that the complementary sections of the needle collector thus formed may enclosed the surgical instruments for disposal; the collector being provided with means for maintaining the collector in a folded condition.

In one embodiment, each rib is folded upon itself in opposite lateral direction to confront adjacent portions of the laminations. In another embodiment, the sponge plastic lamination forms a series of compressed portions between the ribs, the ribs being less dense than the compressed portions therebetween, and the surfaces of the compressed portions may be textured to reduce reflection.

1 Claim, 16 Drawing Figures

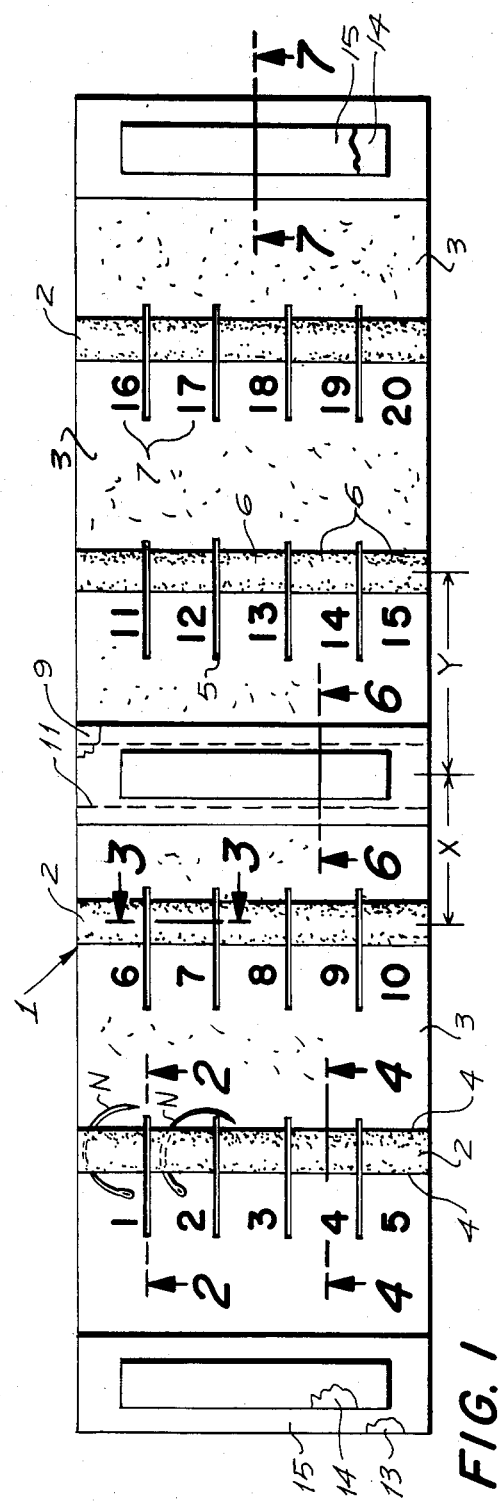
FIG. 1
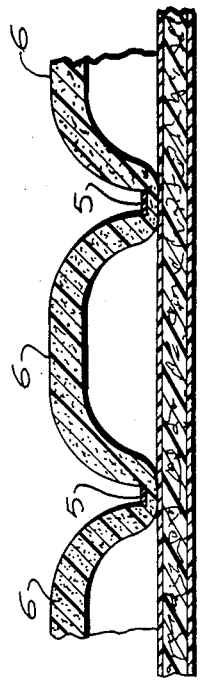
FIG. 2
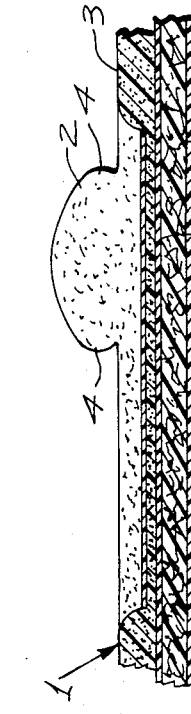
FIG. 4
FIG. 5
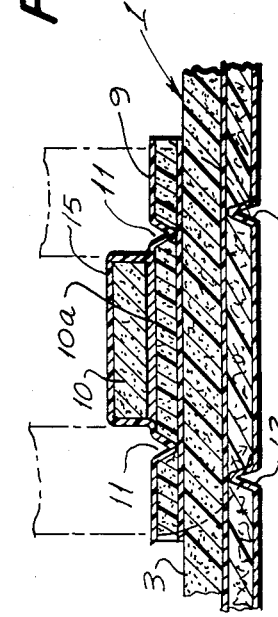
FIG. 3
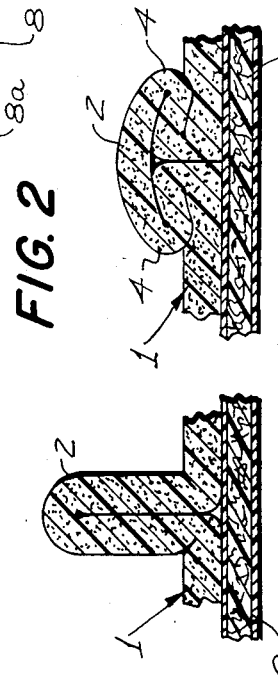
FIG. 6
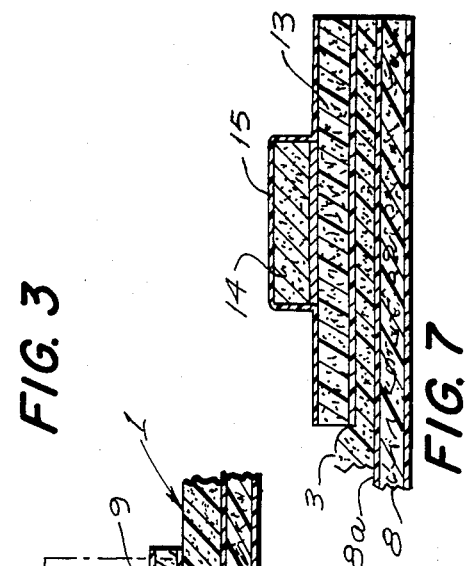
FIG. 7

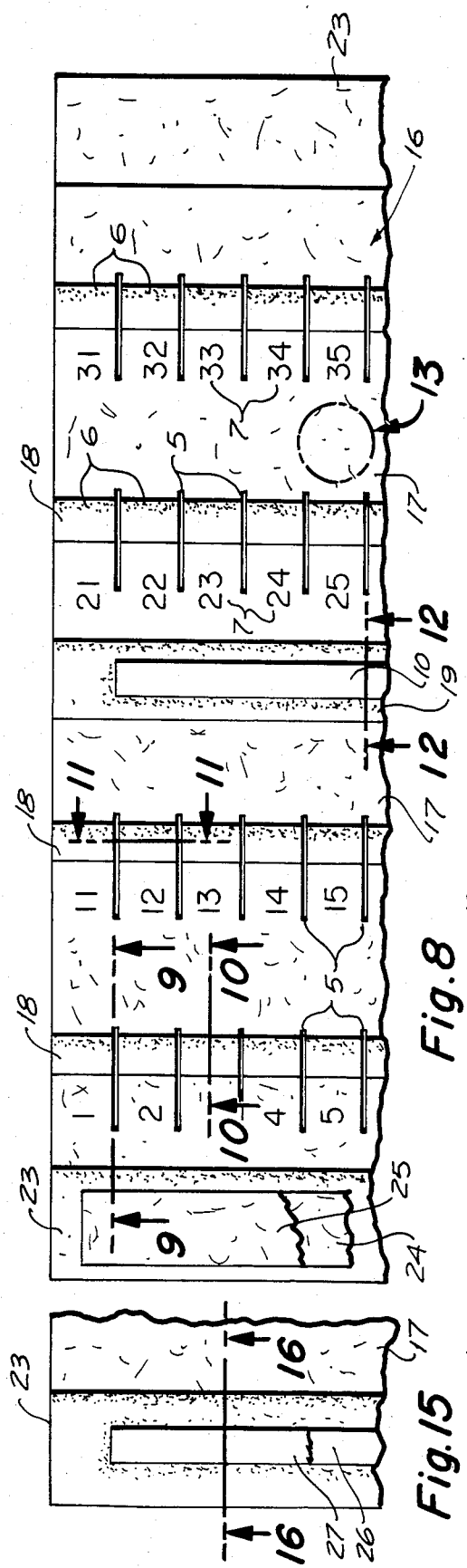
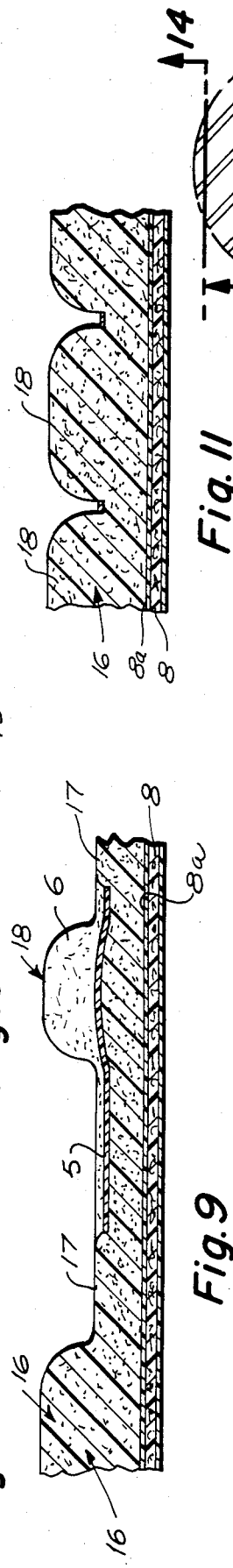
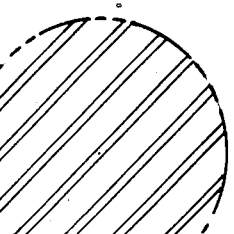
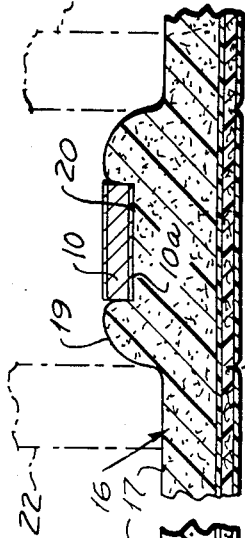
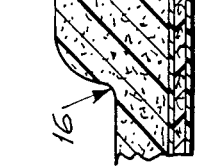
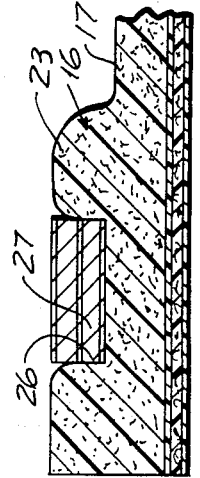

DISPOSABLE SURGICAL IMPLEMENT COLLECTOR

This application is a continuation of application Ser. No. 006,732, filed Jan. 26, 1979, now abandoned, which is a continuation of application Ser. No. 940,399, filed Sept. 8, 1978, now abandoned.

BACKGROUND AND SUMMARY

This invention is a continuation-in-part of application Ser. No. 940,399 filed Sept. 8, 1978, now abandoned and is also related to U.S. Pat. No. 3,727,658 entitled RECEIVER FOR SURGICAL IMPLEMENTS which utilizes a pad provided with magnets for removable retaining small surgical implements during surgery, the pad being foldable to enclose the surgical implements for disposal. This invention is also related to U.S. Pat. No. 3,944,069 entitled Receiver for Disposable Surgical Implements which utilizes a foldable pad providing surfaces having limited adhesiveness so that the implements may be retained thereon during surgery, then the pad is folded for disposal. Both receivers have met with substantial success.

The present invention is directed to the same purpose as the noted patents and is summarized in the following objects:

First, to provide a surgical needle collector which provides a simple and inexpensive means to aid in accounting for a relatively large number of needles or other small surgical implements by provision of a set of areas each clearly marked and identified by a number of other simple marking.

Second, to provide a novel means and method of forming a surgical implement collector wherein one embodiment includes a lamination of foldable material, such as a foamed plastic, material which is folded intermittently to form a series of ribs including lateral portions overlying the lamination.

Third, to provide a novel means and method of forming a surgical implement collector wherein another embodiment includes a lamination of foamed plastic material which is compressed at intervals to provide cross strips of increased density separated by ribs of less density.

Fourth, to provide a novel means and method of forming a surgical implement collector, wherein the ribs are depressed at intervals by appropriate heated means; which divide each rib into a series of readily identifiable embossments, each of which readily receives and retains a surgical instrument.

Fifth, to provide a collector as indicated in the previous objects wherein the foamed plastic lamination is provided with a backing sheet having complementary foldable portions which enclose the foamed plastic lamination to secure the needles or other surgical instrument in the foamed plastic and prevent contact therewith.

Sixth, to provide a collector as indicated in the previous objects wherein magnet strips are provided to maintain the collector in its closed or folded condition and selected magnet strips may be used to temporarily retain surgical blades for repeated use, and to permanently retain blades and enclose them for safe disposal.

BRIEF DESCRIPTION OF THE FIGURES

FIGS. 1 through 7 are directed to one embodiment of the surgical implement collector, in which:

FIG. 1 is a plan view thereof shown in its open condition as it appears when in use.

FIGS. 2, 3 and 4 are enlarged fragmentary sectional views thereof taken respectively through 2—2, 3—3 4—4 of FIG. 1.

FIG. 5 is a fragmentary sectional view corresponding to FIG. 4 showing the rib in its initial position.

FIGS. 6 and 7 are enlarged fragmentary sectional views taken respectively through 6—6 and 7—7 of FIG. 1.

FIGS. 8 through 16 are directed to another embodiment of the surgical implement collector, in which:

FIG. 8 is a fragmentary plan view thereof in its open position when in use.

FIGS. 9, 10, 11, and 12 are enlarged fragmentary sectional views taken through 9—9; 10—10; 11—11; and 12—12 respectively.

FIG. 13 is an enlarged elevational view taken within 13—13 of FIG. 8.

FIG. 14 is a further enlarged fragmentary sectional view taken through 14—14 of FIG. 13.

FIG. 15 is a fragmentary plan view of a modification of the collector.

FIG. 16 is an enlarged fragmentary sectional view taken through 16—16 of FIG. 15.

DETAILED DESCRIPTION

The embodiment of the collector shown in FIGS. 1 through 7 includes a foamed plastic lamination 1 having a series of parallel upwardly extending folded ribs 2 separated by flat areas 3. The foamed character of the lamination extends to its exposed upper surface and its lower surface. That is, the foamed lamination is preferably free of any skin covering its surfaces.

The ribs are expanded laterally from the profile shown in FIG. 5 to the profile shown in FIG. 4, as indicated by 4 in FIGS. 1 and 2. At intervals, the ribs and adjacent portions of the lamination are depressed and simultaneously heated to form a series of transverse depressions 5, dividing each rib into a plurality of readily identifiable embossments 6. The depressions, including their end portions extending beyond the ribs, are darkened or colored in contrast to the remaining portions of the lamination 1. At one side of each rib, between the depressions 5, an appropriate number or other identification marker 7 is formed by pressing an appropriate die into the lamination 1.

The back sides of the flat areas 3 receive a relatively rigid backing plate 8 formed of plastic or cardboard. The lamination 1 is bonded to the backing plate 8 by a conventional adhesive lamination 8a. The backing plate receives midway between its ends a foldable transverse web 9 and a magnet bar 10 having a metal base plate 10a. At opposite sides of the magnet bar 10, the web 9 is provided with fold creases 11 and the backing plate is scored as indicated by 12 so that the two portions of the plate 8 thus formed may be folded as indicated by broken lines in FIG. 6. Each lateral extremity of the backing plate 8 is provided with a transverse reinforcing web 13 and a magnet bar 14. The two magnet bars are mutually engageable; one bar may be merely magnetizable.

The magnet bars 10 and 14 and webs 9 and 13 are covered and bonded together by an adhesive coating 15 which solidifies and forms a protective coating.

Operation of the collector is as follows:

Prior to use, the collector may be stored in a folded condition or in an open position within a sealed envelope, not shown, maintaining the collector in a sterilized condition. When ready for use, the envelope is opened and, if folded, the collector is opened to a flat condition such as shown in FIG. 1. During the course of an operation, a number of needles N or other small surgical implements are used. This is particularly true of needles as each needle is prethreaded and discarded rather than rethreaded. In order to maintain a record of the needle's use, each needle N is inserted laterally into the appropriate embossment 6 in the region corresponding to an identification marker 7. When the operation is completed, the collector is folded and is held closed by the magnet bars 10 and 14. It will be noted that the spacing of the ribs 2 at opposite sides of the web 9 is such that when the backing plate is folded, the ribs carried by the two portions of the backing plate are in offset relation as indicated by "x" and "y" in FIG. 1. It will be noted that the lateral expansion of each embossment 6 causes the portions 4 to fold and confront the lamination 1 and increase the effective width of the embossments.

When the collector is in its open condition shown in FIGS. 1 and 2, the magnet bars 10 and 14 may be used for temporary retention of the needle if further use of the needle is contemplated, it being noted that the collector has been sterilized prior to its use. Also, the magnet bars, particularly the bar 10, may be used to receive small knife blades or the like.

It should be noted that interlocking fiber fastener strips may be used in place of the magnets. For example, but not as a limitation, these strips may be of the type manufactured under the trademark VELCRO. Also, conventional pressure sensitive adhesive strips may be applied to one or both margins, such adhesive strips being covered initially by a paper strip.

While a foamed plastic lamination is preferred, the lamination may be formed of other foldable and pierceable material, such as paper, or may be formed of woven material.

The embodiment of the collector shown in FIGS. 8 through 16 includes a foamed plastic lamination 16 which is heat pressed, by an appropriate die, at intervals to form a set of flat compressed cross strips 17 separated by uncompressed portions forming a set of ribs 18. The respective areas of the cross strips 17 and ribs 18 as well as their relative heights correspond to the areas 3 and ribs 2.

The ribs 18 and adjacent portions of the strips 16 are linearly depressed in the manner also shown in the first embodiment and indicated by 5. The linear depressions divide each rib 18 into a series of readily identifiable embossments 6. As in the first embodiment, the cross strips 17 receive appropriate numbers or other identification markers 7 between the depressions 5.

The lamination 16 is bonded to a backing plate 8 by a conventional adhesive lamination 8a. The lamination 16 is provided midway between its ends with a raised portion 19 similar to the ribs 18, but of greater width. Heat formed in the raised portion 19 is a depression 20 which receives a magnet bar 10 having a metal base plate 10a. At opposite sides of the raised portion 19 fold creases 21 are provided in the backing plate 8 so that the two portions of the backing plate 8 thus formed can be folded into parallel relation as indicated by broken lines 22 in FIG. 12.

Each end of the lamination 16 is provided with an uncompressed or raised portion 23 one of which is provided with a lamination of pressure sensitive adhesive 24 initially covered by a non-adhesive removable lamination 25. Upon removal of the lamination 25 the collector may be folded causing the adhesive lamination to bond the two raised portions 23 so that surgical implements are enclosed. This embodiment is used in the same manner as the first embodiment.

Referring to FIGS. 15 and 16, each raised portion 23 may have a central depression 26 which receives a magnet bar 27.

Referring to FIGS. 13 and 14, the lamination 16 is heat pressed by a die having surface which is textured as indicated by 28. Normally as produce, the surface of a foamed plastic sheet has a reflective surface, which can be troublesome during surgery. By producing a textured surface such surface is essentially non-reflective. Also by compressing the plastic, location of the surface is easier to determine so that the surgical needle or the like can be guided over the compressed surface and into the embossment without snagging the compressed surface.

Having fully described my invention, it is to be understood that I am not to be limited to the details herein set forth, but that my invention is of the full scope of the appended claims.

I claim:

1. A collector for small surgical implements comprising:
    (a) a pair of collector sections hinged to a common web and relatively foldable between a coplanar and a mutually engageable position;
    (b) a magnet carried by the web for receiving surgical implements;
    (c) a plurality of readily penetrable spaced ribs projecting upward from said surfaces;
    (d) means dividing each of the ribs into a series of embossments dimensioned to receive a surgical implement; and
    (e) means attached to said collector for holding said collector sections in mutual engagement.

* * * * *